United States Patent [19]
Abbruzzese et al.

[11] 4,093,727
[45] June 6, 1978

[54] ALPHA-HYDROXYIMINO-ALKYL-QUINOLINIUM SALTS HAVING FUNGICIDE ACTION

[75] Inventors: Luigi Abbruzzese, Milan; Franco Gozzo, S. Donato Milanese (Milan); Giorgio Rossi, Milan; Marcella Masoero, Milan; Simone Lorusso, S. Giuliano Milanese (Milan); Paola Bonola, Milan; Gino Tamburin, S. Donato Milanese (Milan), all of Italy

[73] Assignee: Montedison S.p.A., Milan, Italy

[21] Appl. No.: 677,247

[22] Filed: Apr. 15, 1976

[30] Foreign Application Priority Data

Apr. 15, 1975 Italy .............................. 22346 A/75

[51] Int. Cl.² .................. C07D 215/10; A61K 31/47

[52] U.S. Cl. .............................. 424/258; 260/286 Q
[58] Field of Search ................... 260/286 Q; 424/258

[56] References Cited

U.S. PATENT DOCUMENTS

| 3,878,220 | 4/1975 | Breslow | 260/286 Q |
| 3,970,454 | 7/1976 | Gerbal | 260/243 C |

Primary Examiner—Nicholas S. Rizzo

[57] ABSTRACT

There are disclosed alpha-hydroxyimino-alkyl-quinolinium salts having fungicidal action and, more particularly, alpha-hydroxyimino-alkylquinolinium salts which are active in vivo against Peronospora, Oiduim, Botrytis, against the Fusicladium which attacks apple trees and the rust of the bean plant.

13 Claims, No Drawings

ALPHA-HYDROXYIMINO-ALKYL-QUINOLINIUM SALTS HAVING FUNGICIDE ACTION

THE PRIOR ART

It has been known for some time that 8-hydroxyguinoline exhibits activity as a fungicide; in the form of the sulphate salt is has been used for protecting plants against fungi of the soil (fusiariosi, putrefactions and molds).

However, no practical benefit has been achieved by applying either 8-hydroxyquinoline or its salts to the leaves of plants for protecting the plants against attack by fungi different from the soil fungi.

Also, it is well known that the biological activity of 8-hydroxyquinoline disappears on alkylation thereof with oxygen or nitrogen. (Albert, "Selective Toxicity", 5th Ed., 1973, p. 370 et seq.)

THE PRESENT INVENTION

An object of this invention is to provide new quaternarized quinoline derivatives which are active in vivo against fungine infections.

Another object is to provide a process for preparing the new quaternarized quinoline derivatives.

Still another object is to provide a method for combatting or preventing infections of plants by *Botrytis cinerea, Fusicladium dendriti cum,* and *Sphaerotheca fuliginea* by applying to the plants solutions, suspensions or dispersions, or powders comprising, as the essential anti-fungal agent, the new quaternarized quinoline derivatives.

The active fungicides of the invention have the following general formula:

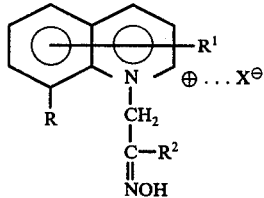

(I)

in which
R is H or OH;
R' is H, a $C_1 \div C_5$ alkyl radical, or a halogen atom;
$R^2$ is CN,

in which $R^3$ is a $C_1 \div C_5$ alkyl radical or a phenyl or substituted phenyl radical; and
$X^-$ is $Cl^-$ or other anion.

The betaine compounds resulting from the elimination of the acid corresponding to the anion $X^-$ from the compounds of formula (I) in which R is OH have also been found by us to exhibit the specific anti-fungal activity, similarly to the compounds of formula (I). The betaine compounds have the general formula:

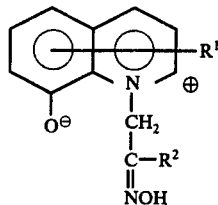

(II)

The salts of general formula (I) in which $X^-$ is $Cl^-$, are prepared by reacting, in a suitable solvent, such as, for example, ethanol or tetrahydrofuran, a quinoline of the general formula:

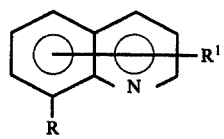

(III)

in which R and R' have the same meanings as given for formula (I), with an alpha-chloromethyloxime of the general formula:

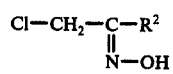

(IV)

wherein $R^2$ has the same meaning as given for formula (I), at room temperature or under mild heating, according to the stoichiometric equation:

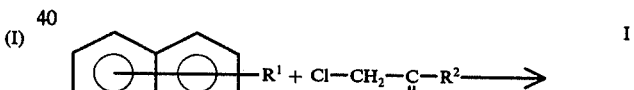

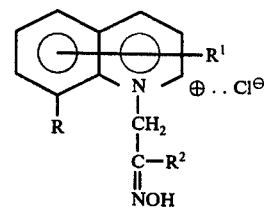

The quinoline salts of formula (I) crystallize spontaneously or by the addition of ethyl ether to the reaction solution. In general, the salts are soluble in water.

The inner quinolinium salts of general formula (II) are obtained by precipitating the salts of formula (I) in which R is OH by addition of alkalis to aqueous solutions of said salts of formula (I). Since this is a reaction regulated by the pH, treatment of the salts of formula II with an acid restores the quaternary salts of formula II with the desired anion:

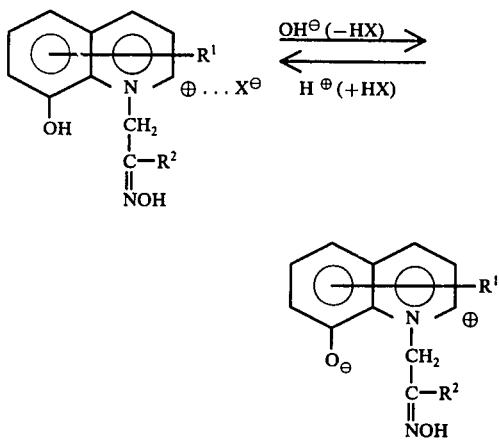

The quinolines of general formula (III) are known in the literature as are, also, the hydroxyoximes of formula (IV) (See K. A. Ogloblin and A. A. Potekhin, "Reaction of Nitrosyl Chloride with Methyl-Vinyl-Ketone and Phenyl-Vinyl-Ketone", Zhurnal Obshehei Khimii, Vol. 34, No. 8, pp. 2688–2693; K. A. Ogloblin and V. P. Semenov, "Reaction with Nitrosyl Chloride with Unsaturated Compounds XXIV — Reaction with Methylacrylate and Acrylonitrile", ibid. Vol. 1, No. 8, pp. 1361–1364; K. A. Ogloblin and A. A. Potekhin, "Reaction of Nitrosyl Chloride with Unsaturated Compounds XXII — Reaction with Unsaturated Alpha-Beta-Aldehydes"; ibid Vol. 1, No. 8, pp. 1352–1356).

We have prepared the following compounds (identified by our code designations) and found them to be biologically active in vivo as fungicides:

M 5224 — 8-hydroxyquinolinium-N-(2-hydroxyimino-butan-3-onyl) chloride; melting point 169°–170° C M 7004 — 8-oxyquinolinium-N-(2-hydroxyimino-butan-3-onyl) betaine; melting point 112°–113° C with decomposition M 6142 — 4-methylquinolinium-N-(2-hydroxyimino-butan-3-onyl) chloride; melting point 196°–197° C M 6195 — 4-methylquinolinium-N-(alpha-hydroxyimino-propionitrile) chloride; melting point 194°–195° C.

M 5223 — quinolinium-N-(alpha-hydroxyimino-proprionitrile) chloride; melting point 182°–183° C

M 6562 — 4-methylquinolinium-N-(alpha-hydroxyimino-propiophenonyl) chloride; m.p. 178°–179° C M 6559 — 8-hydroxyquinolinium-N-(alpha-hydroxyimino-propiophenonyl) chloride; m.p. 139°–141° C.

Both the alpha-hydroxyimino-alkyl-quinolinium salts of formula I as well as the betaines of formula II obtainable from the former, proved capable of preventing infection of useful agricultural plants by noxious fungi; they have also proved capable of curing fungal infections already in progress. The minimum dose of the active anti-fungal agents of the invention for preventing or curing infections by *Botrytis cinerea, Fusicladium dendriticum, Sphaerotheca fuliginea* is 15 micrograms per sq. cm of foliar surface. Larger doeses can be used. The active principle may be applied to the foliage as such, in the form of a powder diluted with inert agents or carriers, or in aqueous or hydroacetonic solution or suspension.

The following examples are given to illustrate the invention and are not intended to be limiting.

EXAMPLE 1

Preparation of 8-hydroxyquinolinium-N-(2-hydroxyiminobutan-3-onyl) chloride.

To a solution of 8-hydroxyquinoline (4.2 g = 9.0293 moles) in absolute ethanol (30 ml), heated up to 40° C and kept under stirring, there was added a solution of 4-chloro-3-hydroxyimino-butan-2-one (4.0 g = 0.0293 moles) in the same solvent (160 ml). The 4-chloro-3-hydroxy-iminobutan-2-one was prepared according to K. A. Ogloblin and A. A. Potekhin Zhurnal Obshchei Khimii, vol. 34, No. 8, pages 2688–2693, August 1964 (CA.61:14519 f).

The solution was kept under stirring for about 1 hour at between 40° and 45° C, and then left to rest at room temperature overnight.

The solid thus formed was filtered, washed with ethyl ether and then dried in the air. Thereby were obtained about 4.8 g of a crystalline, yellow, hydrosoluble solid of m.p. 169°–170° C.

Elementary analysis: Theoretical percentages: C = 55.62%; H = 4.67%; N = 9.98%; Cl$^-$ = 12.63%.
Found percentage: C = 55.85%; H = 4.69%; N = 9.72%; Cl$^-$ = 12.91.

I.R. spectrum: Absorption bands: 3125–2770 cm$^{-1}$; 1695 cm$^{-1}$; 1597 cm$^{-1}$; 1548 cm$^{-1}$; 1374 cm$^{-1}$; 1309 cm$^{-1}$; 1000 cm$^{-1}$; 832 cm$^{-1}$; 760 cm$^{-1}$.

EXAMPLE 2

Preparation of 8-oxyquinolinium-N-(2-hydroxyimino-butan-3-onyl)-betaine.

To an aqueous solution of 8-hydroxyquinolinium-N-(2-hydroxyimino-butan-3-onyl) chloride (2.8 g = 0.01 moles) was added, dropwise and under stirring, a solution of KOH 0.1 N. As the pH attained the value of about 5 there set in the precipitation of the corresponding yellow tinged betaine. This precipitation was completed at pH = 7. The solid was separated by filtering and then dried under vacuum at room temperature, thereby obtaining 2.4 g of solid.

Its behavior under melting, observed by microscope, was characterized by the appearance of a liquid phase at the temperature of 112°–113° C, accompanied by a partial decomposition.

Elementary analysis: Theoretical percentages: C = 63.92%; H = 4.95%; N = 11.47%; Cl = absent; K = absent.

Found percentages: C = 61.72%; H = 4.82%; N = 10.71% Cl absent; K absent. I.R. spectrum: absorption bands: 1678 cm$^{-1}$, 1393 cm$^{-1}$, 1368 cm$^{-1}$, about 1040 cm$^{-1}$ (spread), 828 cm$^{-1}$.

EXAMPLE 3

Preparation of 4-methylquinolinium-N-(2-hydroxyiminobutan-3-onyl) chloride.

To a solution of 4-methylquinoline (5.8 g = about 0.04 moles) in absolute ethanol (30 ml), heated up to 40° C and kept under stirring, there was added a solution of 4-chloro-3-hydroxyimino-butan-2-one (5.4 g = about 0.04 moles) in the same solvent (30 ml).

This solution was kept under stirring for about 2 hours at 40°–45° C and then left to rest at room temperature for one night.

On mixing ethyl ether with the solution, there separated from it a hydrosoluble brown solid having a m.p. of 196°–197° C.

Elementary analysis:

| Theoretical percentage: | Found percentage: |
|---|---|
| Cl⁻ = 12.72% | Cl⁻ = 12.56% |
| N = 10.05% | N = 9.68% |

I.R. spectrum: absorption bands: 2820-2560 cm$^{-1}$; 1701 cm$^{-1}$; 1613 cm$^{-1}$; 1528 cm$^{-1}$; 1022 cm$^{-1}$; 844 cm$^{-1}$; 772 cm$^{-1}$.

EXAMPLE 4

Preparation of 4-methylquinolinium-N-(alpha-hydroxyimino-propionitrile) chloride.

To a solution of 4-methylquinoline (5.8 = about 0.04 moles) in absolute ethanol (30 ml), kept under stirring, there was mixed at room temperature a solution of β-chloro-α-hydroxyiminopropionitrile (4.7 g = about 0.04 moles) in the same solvent (30 ml).

The final solution was obtained at room temperature, under stirring for about 2 hours, and by then allowing it to rest overnight.

The solid thus formed was filtered, washed with ether, then dried in the air. Thereby were obtained about 6.3 g. of a hydrosoluble, brown solid with a m.p. of 194°–195° C.

Elementary analysis
Theoretical percentage: Cl⁻ = 13.55%; N = 16.06%
Found percentage: Cl⁻ = 13.25%; N = 15.58;
I.R. spectrum: Absorption bands: 2820-2560 cm$^{-1}$; 2247 cm$^{-1}$; 1613 cm$^{-1}$; 1538 cm$^{-1}$; 1062 cm$^{-1}$; 795 cm$^{-1}$.

EXAMPLE 5

Preparation of quinolinium-N-(alpha-hydroxyimino-propionitrile) chloride.

To a solution of quinoline (5.0 g = 0.0425 moles) in absolute methanol (20 ml), at room temperature and under stirring, there was mixed a solution of alpha-hydroxyimino-β-chloro-propionitrile (5,5 g = 0.0425 moles) in the same solvent (20 ml).

The alpha-hydroxyimino-beta-chloro-propionitrile was prepared according to K. A. Ogloblin and V. P. Semenov in Zhurnal Organischskoi Khimii, vol. 1, No. 8, pages 1361–1364, August 1965 (C.A. 64; 588a).

The solution was kept under stirring at room temperature for about 2 hours.

The solid that formed was filtered, washed with ethyl ether, then dried in the air. Thereby were obtained about 8.5 g of a white, crystalline solid soluble in water and having a m.p. of from 182° to 183° C.

Elementary analysis
Theoretical percentages: Cl⁻ = 14.21%; N = 17.00%
Found percentages: Cl⁻ = 14.02%; N = 16.82%
I.R. spectrum: absorption bands: 2740-2560 cm$^{-1}$; 2232 cm$^{-1}$; 1631 cm$^{-1}$; 1592 cm$^{-1}$; 1534 cm$^{-1}$; 1055 cm$^{-1}$; 783 cm$^{-1}$.

EXAMPLE 6

Preparation of 4-methylquinolinium-N-(alpha-hydroxyimino-propiophenon-yl)chloride.

To a solution of 4-methylquinoline (4.3 g = about moles in absolute ethanol (30 ml), kept under constant stirring, there was mixed at room temperature a solution of β-chloro-alpha-hydroxyimino-propiophenone (5.9 g = about 0.03 moles) in the same solvent.

The solution was kept at room temperature and under stirring for about 1 hours, then for 30 minutes at 40° C.

On adding ethyl ether at room temperature, there separated a brown oil that subsequently solidified.

The solid, separated by filtering, was washed with ethyl ether and was then dried in the air. Thereby were obtained about 6 g of a product soluble in water. The melting point was 178°–179° C.

Elementary analysis
Theoretical percentage: Cl$^{-1}$ = 10.40%; N = 8.22%
Found percentage: Cl$^{-1}$ = 10.43%; N = 8.48%
I.R. spectrum: Absorption bands: 2670-2380 cm$^{-1}$; 1661 cm$^{-1}$; 1597-1587 cm$^{-1}$; 1520 cm$^{-1}$; 1445 cm$^{-1}$; 780 cm$^{-1}$.

EXAMPLE 7

Preparation of 8-hydroxyquinolinium-N-(alpha-hydroxyimino-propiophenone-yl)chloride.

To a solution of 8-hydroxyquinoline (4.4 g = about 0.03 moles) in absolute ethanol (30 ml), kept under constant stirring, was added a solution of beta-chloro-alpha-hydroxyimino-propiophenone (5.9 g = 0.03 moles) in the same solvent at room temperature.

This solution was then heated to 40° C and kept at this temperature for about 2 hours, then at room temperature overnight. By adding ethyl ether to it, there separated a brown oil which subsequently solidified.

The separated solid was washed with ether and then dried in the air. Thereby there were obtained about 5 g of a product soluble in water and acetone, and having a m.p. of from 139°–141° C.

Elementary analysis
Theoretical percentage: Cl⁻ = 10.34%; N = 8.17%
Found percentage: Cl⁻ = 11.46%; N = 7.75%.
I.R. spectrum: Absorption bands: 3125-2770 cm$^{-1}$; 1653 cm$^{-1}$; 1597 cm$^{-1}$; 1546 cm$^{-1}$; 1370 cm$^{-1}$; 1305 cm$^{-1}$; 1006-1000 cm$^{-1}$; 823 cm$^{-1}$; 753 cm$^{-1}$.

EXAMPLE 8

Determination of the activity

Preventive activity against Botrytis Cinerea Pers. on tomato plants

Both leaf faces of tomato plants cv. Marmande, grown in pots in a conditioned environment, were sprinkled uniformly with a hydroacetonic dispersion at 20% of acetone (vol/vol) containing the products under examination, in three different concentrations until reaching the dripping limit of the leaves.

After one day there was carried out an artificial infection by inoculating both foliar faces with a *Botrytis Cinerea* suspension in carrot broth (1,000,000 spores per cc.).

At the end of the incubation (7 days) the extent of the infection was evaluated by sight by an evaluation scale ranging from 100 (healthy plant) to 0 (completely infected plant). See Table I below.

TABLE I

Preventive Activity Against *Botrytis Cinerea* in Tomato Plants

| | Activity Index (Control = 0) | | |
|---|---|---|---|
| Compound No. | Dose: 0.3% | Dose: 0.15% | Dose: 0.075% |
| 5224 | 100 | 100 | 100 |
| 7004 | 100 | 100 | 100 |
| 6142 | 46 | — | — |
| 6195 | 50 | — | — |
| 5223 | 100 | 100 | 100 |
| 6562 | 60 | — | — |

TABLE I-continued

| | Preventive Activity Against *Botrytis Cinerea* in Tomato Plants | | |
|---|---|---|---|
| | Activity Index (Control = 0) | | |
| Compound No. | Dose: 0.3% | Dose: 0.15% | Dose: 0.075% |
| 6569 | 88 | — | — |

For comparative purposes, tomato plants were treated with a hydroacetonic solution of 0.03% and 0.075%, respectively, of 8-hydroxyquinoline and 8-hydroxyquinolinium sulphate, respectively, and both foliar faces were inoculated with the *Botrytis cinerea* suspension in carrot broth. At 0.3% concentration, the 8-hydroxyquinoline had a preventive activity of 30; at 0.075% concentration its preventive acitvity was zero, as was the finding with respect to the 0.075% solution of 8-hydroxyquinolinium sulphate.

Preventive Activity Against Botrytis Cinerea Pers. on Vines

Both foliar faces of vines cv. Dolcetto, grown in pots in a conditioned environment, were sprayed uniformly with a hydroacetonic dispersion (at 20% by vol. of acetone) containing compound M 5224 in a concentration of 0.15%, until the solution began to drip from the leaves. A statistical survey showed that, under these conditions, the quantity of active substance deposited on the leaves corresponded to an average of 100 μ g/sq. cm of leaf.

After one day, artificial infection was carried out by depositing, on the upper leaf face, 10 drops of a suspension in carrot broth of *Botrytis Cinerea* (1,500,000 of spores per cc.).

At the end of the incubation period (10 days, of which 2 days were in an environment saturated with humidity and 8 days in a conditioned cell at 26° C and 70% relative humidity), the treated plants were found to be completely free from symptoms of disease, while the witness or control plants (not treated) were completely infected.

Curative activity through the leaves on apple trees against Fusicladium dendriticum (Walbr.) Fuck The apple tree leaves cv. Starking, grown in pots in a greenhouse, were uniformly sprayed with an aqueous suspension of *Fusicladium dendriticum conidia* (200,000 conidia per cc.). After 2 days of dwelling in a moisture-saturated environment, said leaves were treated with two of the products under examination in hydroacetonic dispersion (20% vol. of acetone) containing 0.1% of active substance, by spraying the dispersion on both leaf faces.

After an incubation of 14 days, the percentage of foliar surface free from the fungus was visually evaluated according to an evaluation scale ranging from 100 (for the healthy plant) to 0 (for completely infected plant).

TABLE II

| Index of curative activity on apple trees against Fusicladium dendriticum | |
|---|---|
| Compound No. | Dose: 0.1% |
| M 5224 | 72 |
| M 5223 | 63 |

Curative activity through the leaves of cucumber plants on Sphaerotheca fuliginea (Schlech) Salom The leaves of cucumber plants cv. Marketer, grown in pots in a conditioned environment, were uniformly sprayed on the upper leaf face, with an aqueous suspension of *Sphaerotheca fuliginea* (200,000 conidia per cc.); after 24 hours both surfaces of the leaves were sprinkled with a hydroacetonic dispersion of compound 6195 in a concentration of 0.15%.

After an 8-day incubation, the treated plants were found to be completely free of the symptoms of the disease, while the witness or control plants (not treated) were completely infected.

We claim:

1. Alpha-hydroxyimino-akylquinolinium salts of the formula

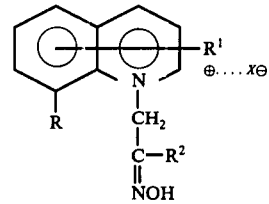

wherein:
R is H or OH;
R¹ is H or alkyl containing 1 to 5 carbon atoms;
R² is CN;

in which R³ is alkyl containing 1 to 5 carbon atoms or phenyl; selected from the group consisting of Cl, Br and I.

2. Betaines resulting from the elimination of the acid corresponding to the anion X⁻ from the compounds of claim 1 in which R is OH and having the formula

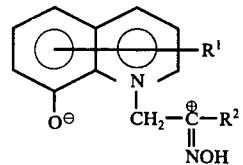

in which
R¹ is H, lower alkyl or halogen; and
R² is CN or O = CR³ in which
R³ is alkyl containing 1 to 5 atoms or phenyl.

3. A compound according to claim 1, characterized in being 8-hydroxyquinolinium-N-(2-hydroxyimino-butan-3-on-yl) chloride or the corresponding betaine.

4. A compound according to claim 1, characterized in being quinolinium-N-(alpha-hydroxyimino-propionitrile) chloride.

5. A compound according to claim 2, characterized in being 8-hydroxyquinolinium-N-(2-hydroxyimino-butan-3-on-yl) betaine.

6. A compound according to claim 1, characterized in being 4-methylquinolinium-N-(2-hydroxyimino-3-on-yl) chloride.

7. A compound according to claim 1, characterized in being 4-methylquinolinium-N-(alpha-hydroxyimino-propionitrile) chloride.

8. A compound according to claim 1, characterized in being 4-methylquinolinium-N-(alpha-hydroxyimino-propiophenyl) chloride.

9. A compound according to claim 1, characterized in being 8-hydroxyquinolinium-N-(alpha-hydroxyimino-propiophenon-yl) chloride.

10. The process for preparing the compounds of claim 1, in which equimolar quantities of a quinoline compound of the formula

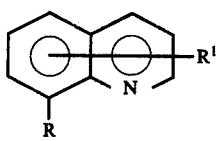

in which
R is H or OH; and
$R^1$ is alkyl containing 1 to 5 carbon atoms, or halogen
are reacted in a solvent, at room temperature of under heating and with stirring, with an alpha-chloroalkyl-hydroxyimine of the formula

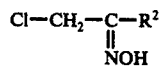

in which
$R^2$ is CN;

in which $R^3$ is alkyl containing 1 to 5 carbon atoms or phenyl.

11. The process of claim 10, in which the solvent is ethanol or tetrahydrofuran, and the reaction is carried out at room temperature or under heating.

12. The process for preparing betaines of claim 2, characterized in that HX is eliminated from N (alpha-hydroxyiminoalkyl) 8-hydroxyquinolinium salts according to the reaction:

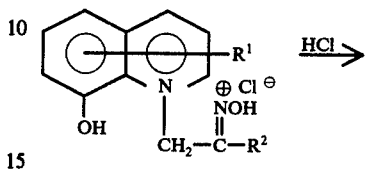

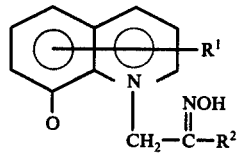

$R^1$ being H, alkyl containing 1 to 5 carbons, or a halogen atom and $R^2$ being CN or

in which $R^3$ is alkyl containing 1 to 5 carbons or phenyl.

13. The method of combatting or preventing fungine infections of plants by *Botrytis cinerea, Sphaerotheca fuliginea* and *Fusicladium dendriticum*, which comprises applying to the plants to be protected powders, suspensions or solutions of the compounds of claim 1, in an amount of at least 15 micrograms per sq. cm of foliar surface.

* * * * *